United States Patent
Schnitzer

(10) Patent No.: US 7,336,988 B2
(45) Date of Patent: Feb. 26, 2008

(54) MULTI-PHOTON ENDOSCOPY

(75) Inventor: Mark J Schnitzer, Hoboken, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 571 days.

(21) Appl. No.: 10/082,870

(22) Filed: Feb. 25, 2002

(65) Prior Publication Data

US 2003/0031410 A1 Feb. 13, 2003

Related U.S. Application Data

(60) Provisional application No. 60/310,917, filed on Aug. 8, 2001.

(51) Int. Cl.
*A61B 6/00* (2006.01)
*G02B 6/04* (2006.01)
*G02B 6/06* (2006.01)

(52) U.S. Cl. .................. 600/476; 600/407; 600/433; 600/434; 600/473; 600/478; 385/115; 385/116; 385/117

(58) Field of Classification Search ............... 600/407, 600/433, 434, 473–478, 101–137, 160–182; 385/115–117
See application file for complete search history.

(56) References Cited

U.S. PATENT DOCUMENTS

| | | | | |
|---|---|---|---|---|
| 3,655,259 | A | | 4/1972 | Miyauchi et al. ............ 359/376 |
| 4,515,444 | A | * | 5/1985 | Prescott et al. ............. 359/654 |
| 4,641,927 | A | * | 2/1987 | Prescott et al. ............. 359/654 |
| 4,723,843 | A | | 2/1988 | Zobel ......................... 350/573 |
| 4,735,491 | A | * | 4/1988 | Takahashi .................... 359/652 |
| 4,880,298 | A | | 11/1989 | Takada ........................ 359/654 |
| 4,905,082 | A | * | 2/1990 | Nishigaki et al. ............. 348/73 |
| 4,916,534 | A | * | 4/1990 | Takahashi et al. .............. 348/67 |
| 5,034,613 | A | | 7/1991 | Denk et al. .................. 250/458 |
| 5,361,166 | A | | 11/1994 | Atkinson et al. ........... 359/654 |
| 5,377,047 | A | | 12/1994 | Broome et al. ............. 359/654 |
| 5,396,366 | A | * | 3/1995 | Brown et al. ............... 359/435 |
| 5,548,113 | A | | 8/1996 | Goldberg et al. ........... 359/368 |
| 5,713,364 | A | * | 2/1998 | DeBaryshe et al. ......... 600/476 |
| 5,804,813 | A | | 9/1998 | Wang et al. .............. 250/201.3 |

(Continued)

FOREIGN PATENT DOCUMENTS

DE 199 27 724 A1 1/2000

(Continued)

OTHER PUBLICATIONS

U.S. Appl. No. 10/029,576, filed Dec. 21, 2001, Schnitzer.

(Continued)

*Primary Examiner*—Brian L. Casler
*Assistant Examiner*—James Kish
(74) *Attorney, Agent, or Firm*—John F. McCabe

(57) ABSTRACT

An apparatus includes an optical element, a GRIN lens, and a detector. The optical element has a first optical aperture. The GRIN lens has first and second ends. The first end of the GRIN lens is positioned to receive light from the first optical aperture. The detector is configured to measure values of a characteristic of light emitted from the first end in response to multi-photon absorption events in a sample illuminated by light from the second end of the endoscopic probe.

21 Claims, 5 Drawing Sheets

U.S. PATENT DOCUMENTS

| | | | |
|---|---|---|---|
| 6,108,094 A * | 8/2000 | Tani et al. | 356/417 |
| 6,166,385 A | 12/2000 | Webb et al. | 250/458.1 |
| 6,169,816 B1 * | 1/2001 | Ravkin | 382/128 |
| 6,341,036 B1 | 1/2002 | Tearney et al. | 359/368 |
| 6,542,665 B2 * | 4/2003 | Reed et al. | 385/34 |
| 6,663,560 B2 * | 12/2003 | MacAulay et al. | 600/160 |

FOREIGN PATENT DOCUMENTS

| | | |
|---|---|---|
| WO | WO 94/07142 | 3/1994 |
| WO | WO 98/38907 | 9/1998 |
| WO | WO 99/44089 | 9/1999 |
| WO | WO 01/59423 A2 | 8/2001 |
| WO | WO 02/48688 A1 | 6/2002 |

OTHER PUBLICATIONS

U.S. Appl. No. 09/919017, filed Jul. 31, 2001, Reed et al.

EPO Search report for EPO patent Application, 0225132.9, Dec. 20, 2002, 5 pages.

"Research Reduces Cost of Endoscopes," Optics and Laser Technology, Elsevier Science Publishers BV., Amsterdam, NL, vol. 25, No. 6, Dec. 1, 1993, p. 400.

* cited by examiner

MULTI-PHOTON ENDOSCOPY

This application claims the benefit of U.S. Provisional Application No. 60/310,917, filed Aug. 8, 2001.

BACKGROUND

1. Field of the Invention

This invention relates to optical endoscopy.

2. Discussion of the Related Art

Multi-photon imaging exploits non-linear optical properties of a sample to create an image of the sample. One type of multi-photon imaging is two-photon fluorescent microscopy in which scanning light causes portions of a sample to fluoresce as a result of two-photon absorption events in the sample. Other types of multi-photon imaging use other multi-photon processes, e.g., three-photon fluorescence, second- or third-harmonic generation, and Raman absorption, to create images. These multi-photon processes enable producing scanned images of samples.

Imaging techniques based on nonlinear optical properties have several common features. One common feature is that the produced images depend on the chemical composition of a sample. Thus, the images enable extracting data on a sample's chemical composition, i.e., data that may not be available through imaging techniques based on linear optical processes. Another common feature is the use of lower energy photons than in imaging techniques based on linear optical processes. Lower energy photons are used, because more than one photon provides the excitation energy for the nonlinear optical processes. The lower energy photons have longer wavelengths that typically penetrate better in dense sample media such as biological tissue. Another common feature is that the optical imaging events have smaller optical cross-sections than those used in imaging techniques based on linear optical processes. The smaller optical cross-sections usually necessitate higher illumination intensities than in the imaging techniques based on linear optical processes. For the higher illumination intensities, non-linear optical imaging systems typically rely on ultra-fast pulsed lasers, e.g., pulsed femto-second or pulsed pico-second lasers.

Pulses from such ultra-fast pulsed laser sources are susceptible to degradation by dispersion and non-linear optical processes that occur in imaging instrumentation. Dispersion and non-linear optical processes produce temporal and spectral alterations of optical pulses. These degradative effects reduce the ability of the pulses to generate multi-photon events in a sample. Although dispersion can be pre-compensated, non-linear optical processes are usually not amenable to pre-compensation. For that reason, the non-linear processes interfere with multi-photon imaging techniques and have impeded the use of optical endoscopes in multi-photon imaging.

SUMMARY

Degradation by non-linear optical processes in single mode optical fibers interferes with the use of optical pulses in multi-photon imaging. To avoid such degradation, various embodiments of probes use graded refractive index (GRIN) lenses, i.e., lenses with radially graded refractive indexes, to deliver illumination light to samples. The GRIN lenses have larger core diameters than single-mode optical fibers. The larger core diameters of the GRIN lenses reduce light intensities so that cross sections for non-linear optical processes are not as large as those in probes that are based on single-mode optical fibers or arrays of single-mode fibers.

In one aspect, the invention features an apparatus that includes an optical element, a GRIN lens, and a detector. The optical element has a first optical aperture. The GRIN lens has first and second ends. The first end of the GRIN lens is positioned to receive light from the first optical aperture. The detector is configured to measure values of a characteristic of light emitted from the first end of the GRIN lens in response to multi-photon absorption events in a sample illuminated by light from the second end of the GRIN lens.

Some embodiments use long GRIN lenses, e.g., longer than 1 centimeter. These GRIN lenses are long enough to receive illumination light at an end face located outside a sample and emit light from a second end face located deep below the surface of the sample.

In another aspect, the invention features a process for scanning a region of a sample. The process includes positioning a first end face of a GRIN lens near the region of the sample, transmitting light to a second end face of the GRIN lens, and scanning the incidence position or angle of the light on the second end face. The scanning and transmitting are performed together to generate a scan of the region of the sample.

DETAILED DESCRIPTION OF EMBODIMENTS

Various embodiments of include probes designed for insertion into a sample or body, i.e., endoscopic probes. The endoscopic probes transport light used to illuminate and scan the sample and collect light emitted by the sample. The emitted light is used to produce a scanned image of a portion of the sample.

Figure 1A:
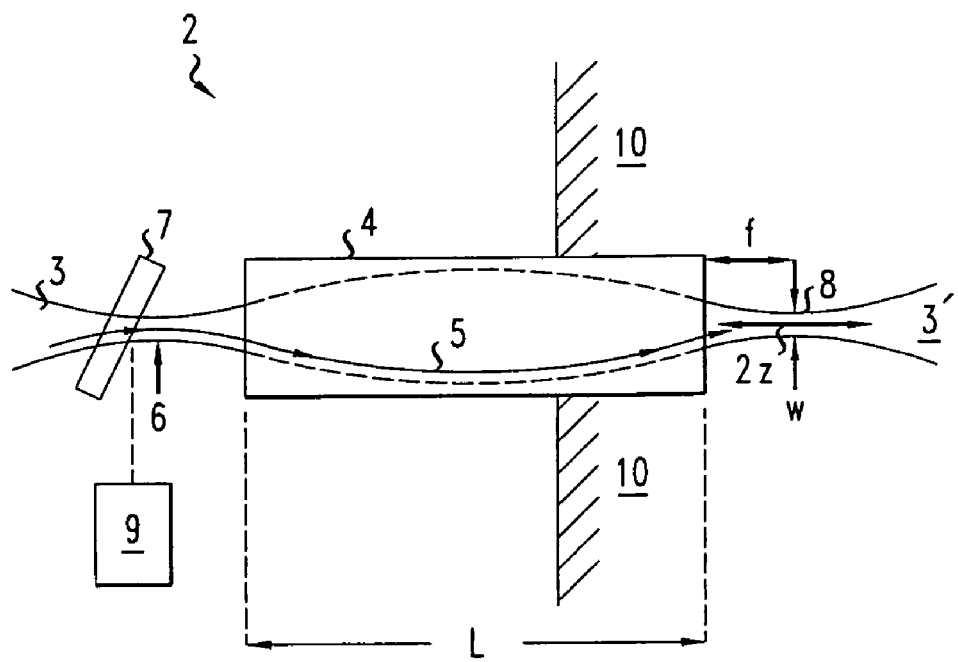
FIG. 1A is a cross-sectional view of an endoscopic probe with a GRIN lens whose length is less than a ½ pitch.

FIG. 1A shows an endoscopic probe 2 that is based on a GRIN lens 4. The GRIN lens 4 delivers laser light pulses to the interior of sample 10. The laser light pulses provide illumination for producing scanned multi-photon images of the sample 10. The GRIN lens 4 has a cylindrical cross section and a radially graded refractive index profile. Exemplary GRIN lenses 4 include cylindrical lenses having diameters in the range of about 0.125 millimeters (mm) to about 3 mm and optical GRIN fibers.

The GRIN lens 4 has a refractive index profile whose radial variation bends light rays 5 propagating therein.

Exemplary refractive index profiles have parabolic or hyperbolic secant dependencies on the distance from the axis of the GRIN lens 4. Inside the GRIN lens 4, light rays 5 follow an approximately sinusoidal path about the GRIN lens' central axis.

Herein, the pitch length of a GRIN lens refers to the lens length as measured along the lens axis in full periods of a ray's trajectory in the GRIN lens. In a GRIN lens of pitch length one, the diameter of a light beam undergoes two full oscillations while propagating through the lens. For a GRIN lens, the pitch is the length of the lens material that would produce two full oscillations in a light beam's width, and so pitch length is the length in units of pitch. A first GRIN lens bends light rays more strongly than a second GRIN lens if the first GRIN lens has a shorter pitch than the second GRIN lens.

Various endoscopic probes use propagation and focusing properties of GRIN lenses to reduce undesirable nonlinear effects on transported light pulses. In particular, the sinusoidal variation of a light beam's diameter in a GRIN lens implies that light intensities are lower along at least part of the ray path, i.e., along path portions away from the central axis of the GRIN lens. Since non-linear effects require high light intensities, such effects are less probable in GRIN lenses than in single-mode optical fibers, because a portion of a ray's path in a GRIN lens is typically in a region where light intensities are lower. For this reason, nonlinear effects typically produce less change in a pulse's-shape in GRIN lenses than in single-mode optical fibers of equal length.

To use endoscopic probe 2, an illumination optical beam 3 is focused into GRIN lens 4. The illumination beam 3 forms a focal waist 6 near or on an end face of the GRIN lens 4 that is external to sample 10. The GRIN lens 4 has a length of slightly less than ½ pitch so that the endoscopic probe emits a beam 3' that forms second focal waist 8 near another end face of the GRIN lens 4. The second focal waist 8 is located below the surface of the sample 10 and at a distance, f, from the end face of the GRIN lens 4. The distance, f, defines the distance of the end face of the GRIN lens 4 from the focal plane scanned during multi-photon imaging.

In response to being illuminated by GRIN lens 4, sample spots emit light. A portion of the emitted light is collected by the GRIN lens 4, which delivers the light to a dichroic slab 7. The dichroic slab 7 transmits illumination light and reflects light emitted by the sample 10. Thus, the dichroic slab 7 deflects the light that the GRIN lens 4 collects from the sample 10 to an external optical detector 9. The detector 9 measures an optical characteristic of the collected emitted light, e.g., intensity or phase. The measured characteristic provides data for producing a scanned image of the portion of the sample 10 that emitted the light.

Since multi-photon absorption events require high light intensities, the probability of such events is low in regions where light intensities are low. For endoscopic probe 2, multi-photon events are rare in regions of the sample 10 distant from the focal waists 6, 8, i.e., the regions of high relative light intensity. Thus, multi-photon absorptions cause light emission from portions of the sample 10 that are located at the focal spot. At the focal spot, the beam has a waist, w, and a Rayleigh range, z. The quantities w and z determine the respective lateral and depth resolutions in multi-photon imaging.

Exemplary GRIN lenses 4 have lengths L that are shorter than or equal to ½ pitch. The length L determines the depth that the endoscopic probe 2 of FIG. 1A can be inserted into sample 10. Typical ½ pitch lenses have lengths, L, with values in the range of about 500 microns to 5 centimeters. L is preferably equal to about 1 centimeter or more.

A GRIN lens whose pitch-length is less than ½ does not have internal focal waists where light intensities would become relatively high due to beam focusing. Thus, a GRIN lens with a pitch length of less than ½ keeps internal light intensities low and reduces undesired non-linear optical effects inside the GRIN lens. Such effects could otherwise degrade the quality of optical pulses transmitted by the GRIN lens and thus, degrade the quality of such pulses for multi-photon scanning.

Some endoscopic probes use GRIN lenses with pitch lengths longer than ½. These endoscopic probes are able to image regions located deeper below a sample's surface, because the GRIN lenses delivering the illumination light are longer. But, the longer GRIN lenses also have at least one internal focal waist, i.e., located inside the GRIN lens. At the internal focal waist, multi-photon events are more probable due to the relatively increased light intensities. Thus, multi-photon imaging systems based on the longer GRIN lenses are more susceptible to pulse broadening due to non-linear optical effects. Nevertheless, nonlinear effects cause less degradation of pulses in the longer GRIN lenses than in single-mode optical fibers of equal length, because light intensities are only high at internal focal waists in the GRIN lenses. In single-mode optical fibers light intensities are high along the entire length of the fiber. Using a GRIN lens rather than a single-mode optical fiber reduces broadening of illumination pulses during delivery of the pulses to the sample 10 to be scanned.

While longer GRIN lenses produce a small increase in undesirable non-linear effects such as self-phase modulation, the longer GRIN lenses enable manufacture of longer endoscopic probes. Exemplary GRIN lenses produce endoscopes with lengths of 30-200 millimeters without significantly degrading short optical pulses through non-linear processes. The low degradation results because multi-photon effects are limited to short focal waist regions in the GRIN lenses.

Figure 1B:
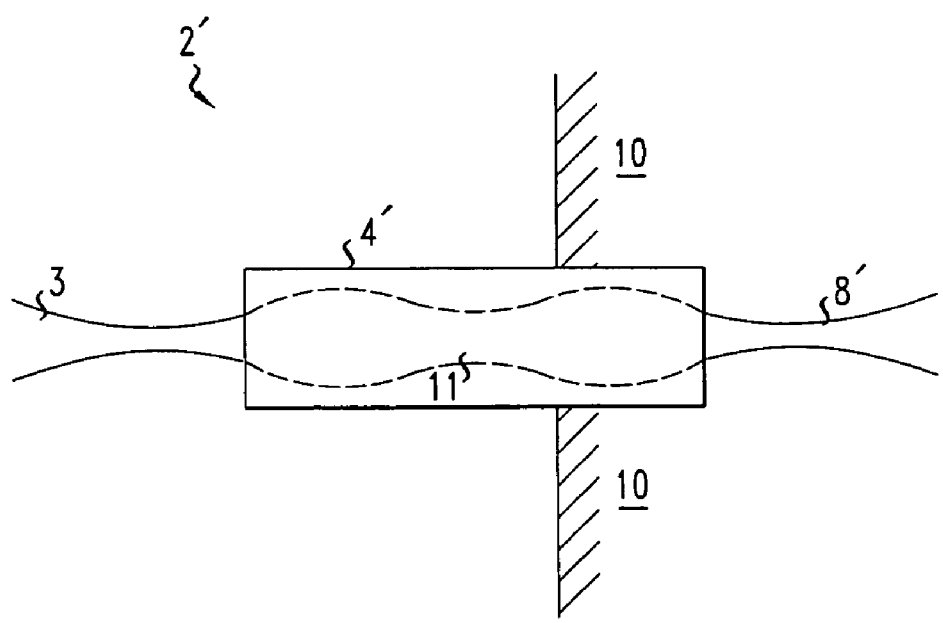
FIG. 1B is a cross-sectional view of an endoscopic probe with a GRIN lens whose length is longer than a ½ pitch.

FIG. 1B shows a longer endoscopic probe 2', which is based on a GRIN lens 4' with a pitch-length of between about 0.75 and about 1. The GRIN lens 4' is either a cylindrical GRIN lens or an GRIN optical fiber. The GRIN lens 4' has an internal focal waist 11 and an external focal waist 8', which is located in the sample 10. Since the GRIN lens 4' is longer than GRIN lens 4 of FIG. 1A, the GRIN lens 4' produces more chromatic dispersion of optical pulses. The chromatic dispersion can be reduced by pre-compensation techniques known to those skilled in the art.

In GRIN lenses, the oscillatory variations in beam diameter diminish with length of the GRIN. Thus, focusing ability degrades as the length of the GRIN lens increases. To reduce such degradation, some endoscopic probes use weak GRIN lenses, i.e., GRIN lenses with long pitches, e.g., between about 1 millimeter and 1 decimeter. An endoscopic probe, which is based on a weak GRIN lens, can be long and still have a length that is only be only a few times the pitch of the GRIN lens. Such an endoscopic probe includes few internal focal waists where pulse degradation occurs. Nevertheless, these weak GRIN lenses also have long Rayleigh ranges and focal depths. The long focal lengths and Rayleigh ranges reduce the maximum light intensities achievable at external focal waists and the depth-selectivity of images, i.e., the ability to make optically sectioned images. Long focal lengths are also undesirable for imaging of sample regions that are close to the end of the GRIN lens, i.e., within a few hundred microns.

Figure 1C:
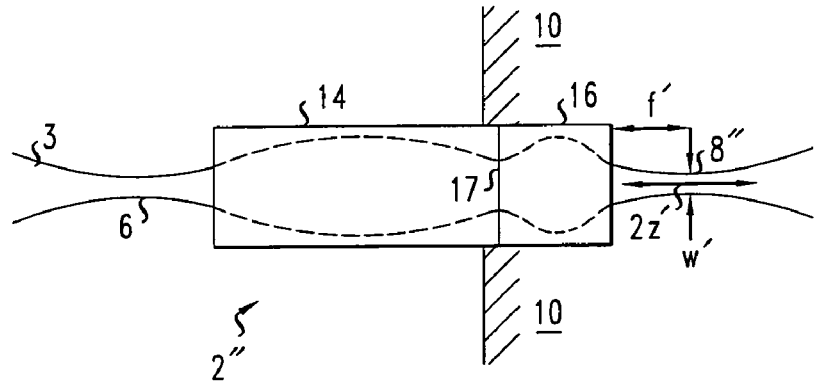
FIG. 1C is a cross-sectional view of an endoscopic probe with a compound GRIN lens.

FIG. 1C shows an endoscopic probe 2" that uses a compound GRIN lens to overcome some of the problems associated with weak GRIN lenses. The compound GRIN lens serially combines a relay GRIN lens 14, i.e., a weak GRIN lens, and an objective GRIN lens 16, i.e., a relatively stronger GRIN lens. The relay and objective GRIN lenses 14, 16 are cylindrical GRIN lenses or GRIN optical fibers. The relay GRIN lens 14 has a longer pitch than the objective GRIN lens 16, e.g., five or more times longer. The objective GRIN lens 16 is stronger and has a shorter focal length, f', than the relay GRIN lens 14, e.g., f'$\leq$1 mm. The relay GRIN lens 14 also forms a longer portion of the endoscopic probe 2" than the objective GRIN lens 16. Exemplary relay GRIN lenses 14 are at least 0.5 cm long and are preferably, at least, 1-5 cm or more long or longer, e.g., 5-100 cm long.

During data collection, the objective GRIN lens 16 is positioned beneath the surface of sample 10. The objective GRIN lens 16 focuses illumination light at focal waist 8" in a manner that is similar to a microscope objective lens. The objective GRIN lens 16 produces a small external focal waist, w', and a small depth of focus, 2z', i.e., w' and 2z' are smaller than about one 1 micron and about 3 microns, respectively. The small values for w' and 2z' produce high illumination intensities at the focal waist 8", i.e., intensities high enough for multi-photon imaging and depth sectioning.

Since objective GRIN lens 16 is stronger than relay GRIN lens 14, the objective GRIN lens 16 has a higher numerical aperture than the relay GRIN lens 14. Thus, some of the light collected by objective GRIN lens 16 may not propagate in the relay GRIN lens 14. In particular, collected light that makes a larger angle with the normal vector to interface 17 than the acceptance angle for the relay GRIN lens 14 does not propagate therein. The converse is true for the excitation light, i.e. the light delivered from the relay lens 14 will not fill the acceptance cone of the objective lens 16. Thus, then the numerical aperture of the objective GRIN lens 16 does not of itself fix the maximum image resolution for endoscopic probe 2".

Figure 1D:
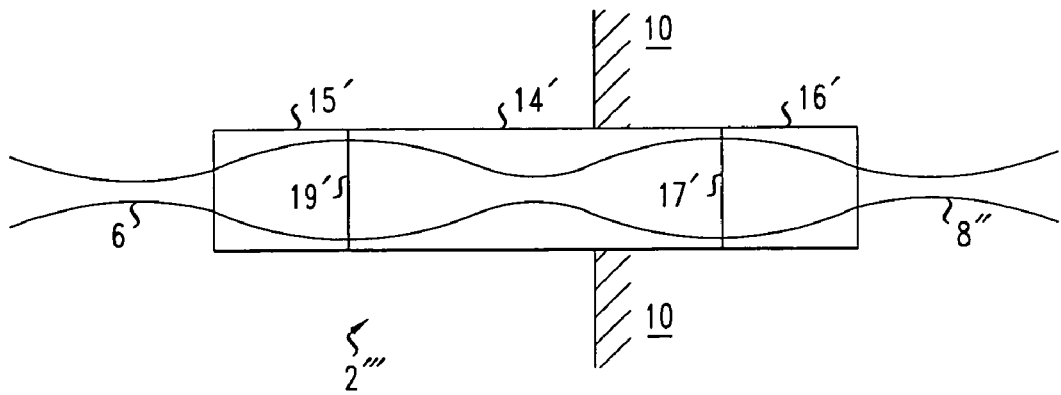
FIG. 1D is a cross-sectional view of an alternate endoscopic probe with a compound GRIN lens.

FIG. 1D shows an endoscopic probe 2''' whose coupling to external optical sources is not significantly limited by properties of relay GRIN lens 14'. The endoscopic probe 2''' serially combines the relay GRIN lens 14' with coupling GRIN lens 15' and objective GRIN lens 16'. The coupling and objective GRIN lenses 15', 16' have larger numerical apertures than the relay GRIN lens 14'. Nevertheless, light collected by the coupling or objective GRIN lens 15', 16' is not significantly lost at interfaces 19', 17' with the relay GRIN lens 16, because the light is collimated at the interfaces 19', 17'. To collimate light incident on the interfaces 17', 19', the interface 17' and the interface 19' are configured to be the Fourier conjugates to focal waist 8" and focal waist 6, respectively. Since the light is collimated at the interfaces 17', 19', the entire cones of light, which are collected by the coupling and objective GRIN lenses 15', 16', propagate in the relay GRIN lens 14'. For this reason, the numerical aperture of the objective GRIN lens 16' alone determines the image resolution. Similarly, the numerical aperture of the coupling GRIN lens 15' alone determines the efficiency of the coupling between the endoscopic probe 2''' and an external pulsed laser source (not shown). In particular, the numerical aperture of the coupling GRIN lens 15' can be selected so that no significant insertion losses occur even when a larger numerical aperture lens focuses a light beam from the pulsed laser source onto the end face of the endoscopic probe 2'''.

Some endoscopic probes scan regions of samples lateral to the probes.

Figure 1E:
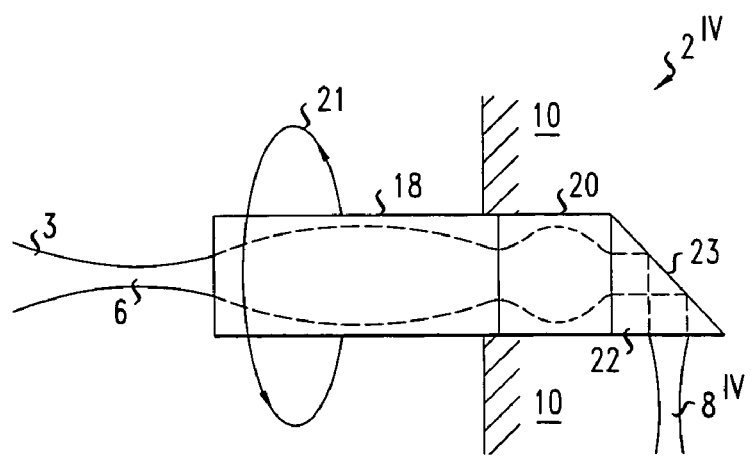
FIG. 1E is a cross-sectional view of an endoscopic probe with a compound GRIN lens and a prism.

FIG. 1E shows an endoscopic probe $2^{IV}$ that scans portions of sample 10 lateral to the probe $2^{IV}$. The probe $2^{IV}$ includes a relay GRIN lens 18, an objective GRIN lens 20, and an optical prism 22. The optical prism 22 has a face 23 that is oriented at an angle with respect to the central axis of the endoscopic probe $2^{IV}$. Exemplary face angles are in the range of about 15 degrees to about 75 degrees. The angling of the face 23 causes the prism 22 to deflect an illumination beam at an angle to the axis of the endoscopic probe $2^{IV}$ thereby illuminating a lateral portion of the sample 10. The prism 22 also collects light emitted from the same lateral regions of the sample 10. By rotating the probe $2^{IV}$ about its axis, an operator is able to change the lateral region of sample 10 illuminated and imaged by the endoscopic probe $2^{IV}$, i.e., by changing the lateral position of beam waist $8^{IV}$.

Since multi-photon imaging systems scan a region of a sample to acquire image data, these imagining systems scan illumination spots over the region of the sample being imaged.

Figure 2A:
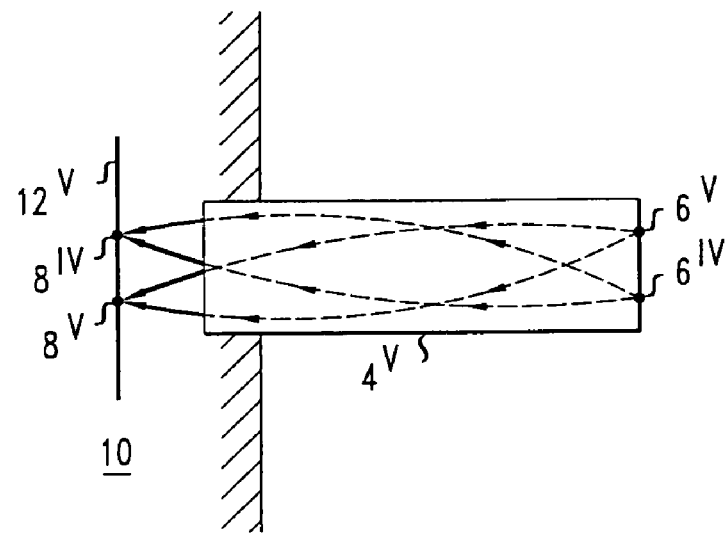
FIG. 2A shows how scanning incident light over one face of an endoscopic probe produces a scan in a focal plane located in a sample.
Figure 2B:
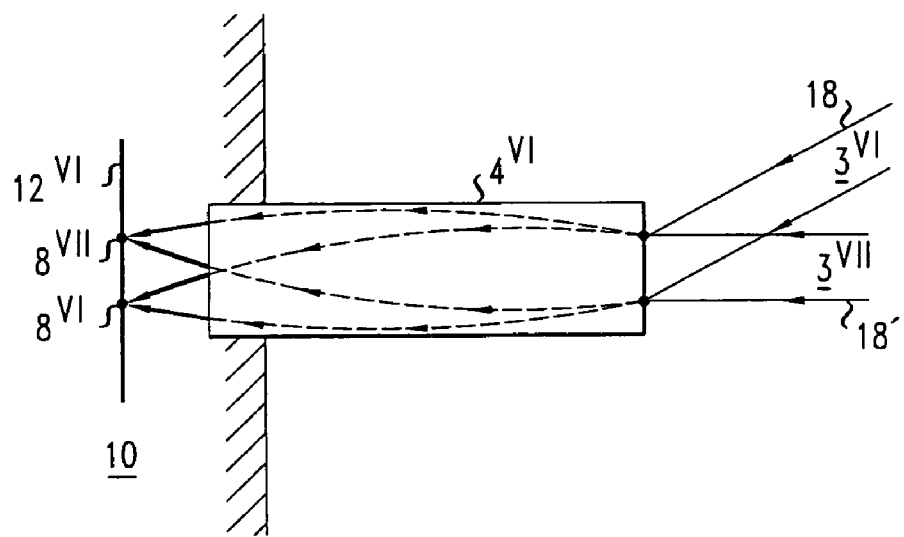
FIG. 2B shows how pivoting the direction of incident light on one face of an endoscopic probe produces a scan in a focal plane located in a sample.

FIGS. 2A and 2B illustrate methods for scanning a sample with an endoscopic probe based on a simple GRIN lens, e.g., probes 2, 2' of FIGS. 1A and 1B. Adapting these methods to enable sample scanning with endoscopic probes 2", 2''', $2^{IV}$ of FIGS. 1C, 1D, and 1E will be clear to those skilled in the art.

In FIG. 2A, a focused light beam scans an external end face of the GRIN lens $4^V$. From each spot of light $6^{IV}, 6^V$ on the external end face, the GRIN lens $4^V$ produces a second focused spot of light $8^{IV}, 8^V$ in a plane $12^V$ in sample 10. Thus, scanning the external end face of the GRIN lens $4^V$ produces a scan of a portion of the sample 10 on plane $12^V$. Exemplary GRIN lenses $4^V$ have total pitch lengths in the range of ¼ to ½ modulo a half-integer. The numerical aperture of GRIN lens $4^V$ should be large enough to accept the entire cone of light incident on its external end face in order that light for exciting multi-photon processes is not lost at the external end face.

An alternate scanning method, which avoids the need for a coupling lens to preserve resolution, is shown in FIG. 2B. In FIG. 2B, pivoting the incidence angle of a collimated illumination beam $3^{VI}, 3^{VII}$ on the external face of GRIN lens $4^{VI}$ produces scanning. Pivoting the incidence orientation of the illumination beam $3^{VI}, 3^{VII}$ between direction 18 and direction 18' causes a focused spot to scan the sample 10 from point $8^{VI}$ to point $8^{VII}$ on the focal plane $12^{VI}$ of the GRIN lens $4^{VI}$. The area that the illumination light beam strikes on the external face of GRIN lens $4^{VI}$ remains approximately constant during the pivoting action that produces the scanning. Exemplary GRIN lenses $4^{VI}$ have a pitch-length in the range of 0 to ¼ modulo a half-integer.

Figure 3:
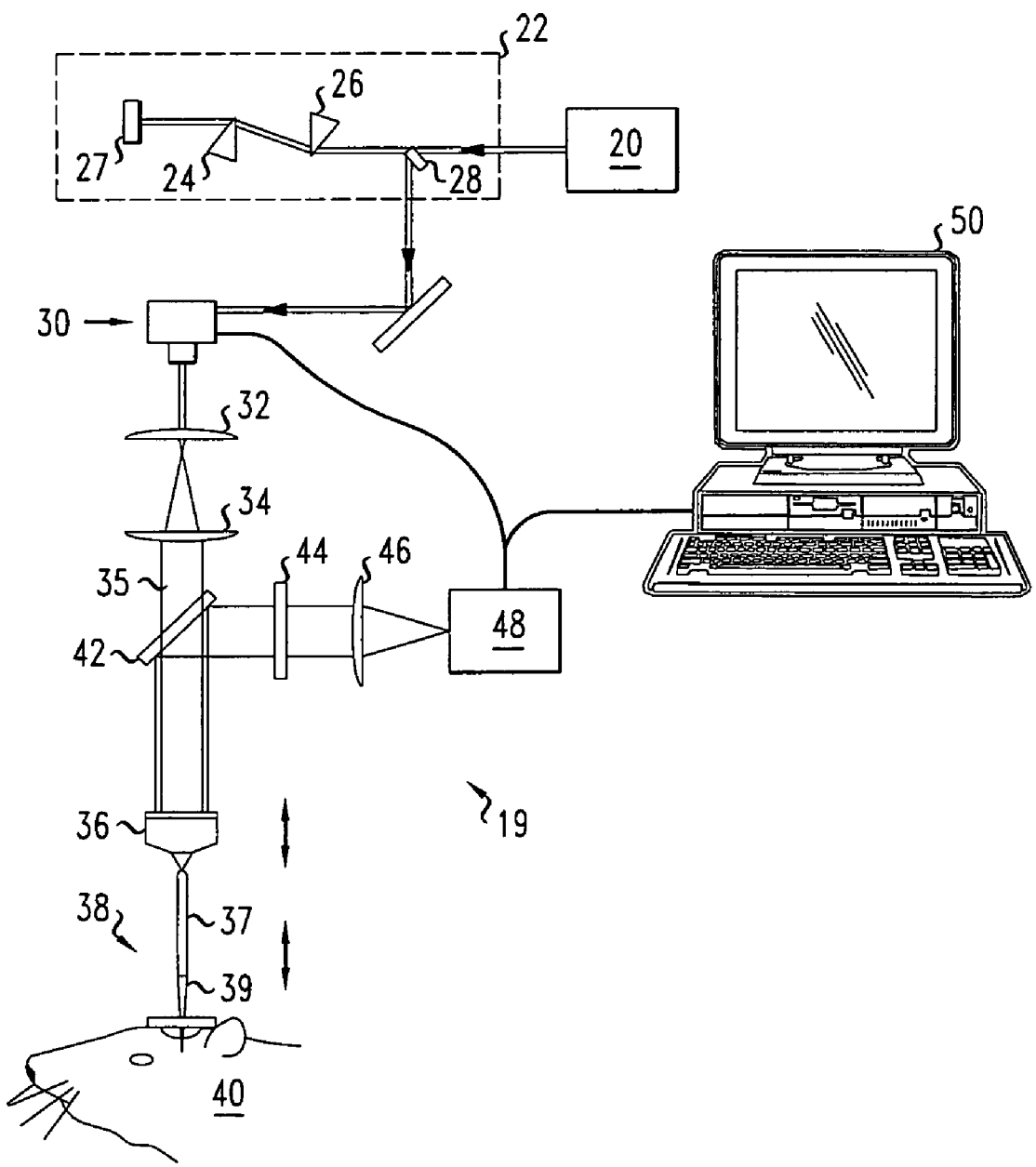
FIG. 3 is a block diagram of a multi-photon endoscopic imaging system.

FIG. 3 shows a scanning system 19 that uses two-photon absorption events to produce a scanned image of a portion of sample 40. The scanning system 19 includes a pulsed laser 20 that provides the high intensity optical pulses needed to generate two-photon absorption events in the sample 40. Exemplary pulsed lasers 20 include ultra-fast pulsed Ti-sapphire laser that produce femto-second or pico-second pulse lengths. The pulsed laser 20 sends the optical pulses to a compensator 22 that pre-compensates for chromatic dispersion. The compensator 22 sends the pre-compensated optical pulses to an optical delivery system, which transmits the pulses to endoscopic probe 38. The endoscopic probe 38 includes a relay GRIN lens 37 and an objective GRIN lens 39, e.g., endoscopic probe 2" of FIG. 1C. The endoscope probe 38 delivers the high intensity optical pulses to the portion of the sample 40 to be scanned.

The compensator 22 includes a pair of Brewster angle prisms 24, 26, a reflector 27, and a pick off mirror 28. The compensator 22 functions as a double-pass device, in which light passes through each prism 24, 26 twice. The pick-off mirror 28 deflects a portion of the beam of pre-compensated pulses from the compensator 22 and sends the deflected portion of the beam to the optical delivery system.

The optical delivery system includes a pair of x-direction and y-direction beam deflectors 30, telescopic pair of lenses 32, 34, a dichroic mirror 42, and an insertion lens 36.

Exemplary x, y-direction beam deflectors 30 include galvanometer-controlled mirrors, acousto-optic deflectors, and electro-optic deflectors. The x-direction and y-direction beam deflectors 30 steer the beam in perpendicular lateral directions thereby producing a two-dimensional scan of a portion of sample 40. A programmable computer 50 controls the x-direction and y-direction beam deflections that are generated by beam deflectors 30. Thus, the computer 50 controls sample scanning in directions lateral to the beam direction.

From beam deflectors 30, optical pulses pass through a telescopic pair of lenses 32, 34 that expand the beam diameter to produce an expanded illumination beam 35. The expanded beam 35 passes through dichroic mirror 42 and is transmitted to insertion lens 36, i.e., a high numerical aperture lens. The diameter of the expanded beam 35 matches the entrance pupil of the insertion lens 36. The insertion lens 36 focuses the expanded illumination beam 35 to a spot on or near the external end face of endoscopic probe 38.

The imaging system 19 has a dual focus mechanism (not shown) that enables independently adjusting the distance between endoscopic probe 38 and the surface of sample 40 and the distance between insertion lens 36 and the endoscopic probe 38. The dual focusing mechanism enables fine adjustments of the depth of the probe's focal plane in the sample 40 without requiring movements of the endoscopic probe 38 itself.

Portions of sample 40 emit light in response to two-photon absorption events. Part of the emitted light is recollected by endoscopic probe 38, which delivers the collected light to insertion lens 36. From the insertion lens, dichroic mirror 42 deflects the collected light to a chromatic filter 44. The chromatic filter 44 removes wavelengths outside the emission spectrum of the sample 40 and delivers the remaining light to a focusing lens 46. The focusing lens 46 focuses the remaining light onto a photo-intensity detector 48, e.g., a photomultiplier or avalanche photodiode. The photo-intensity detector 48 produces an electrical signal indicative of the intensity of the received light and transmits the electrical signal to computer 50, i.e., a data processor and controller. The computer 50 uses intensity data from the photo-intensity detector 48 and data on the x- and y-deflections of the illuminating beam 35 to produce a scan image of the sample 40.

Figure 4:
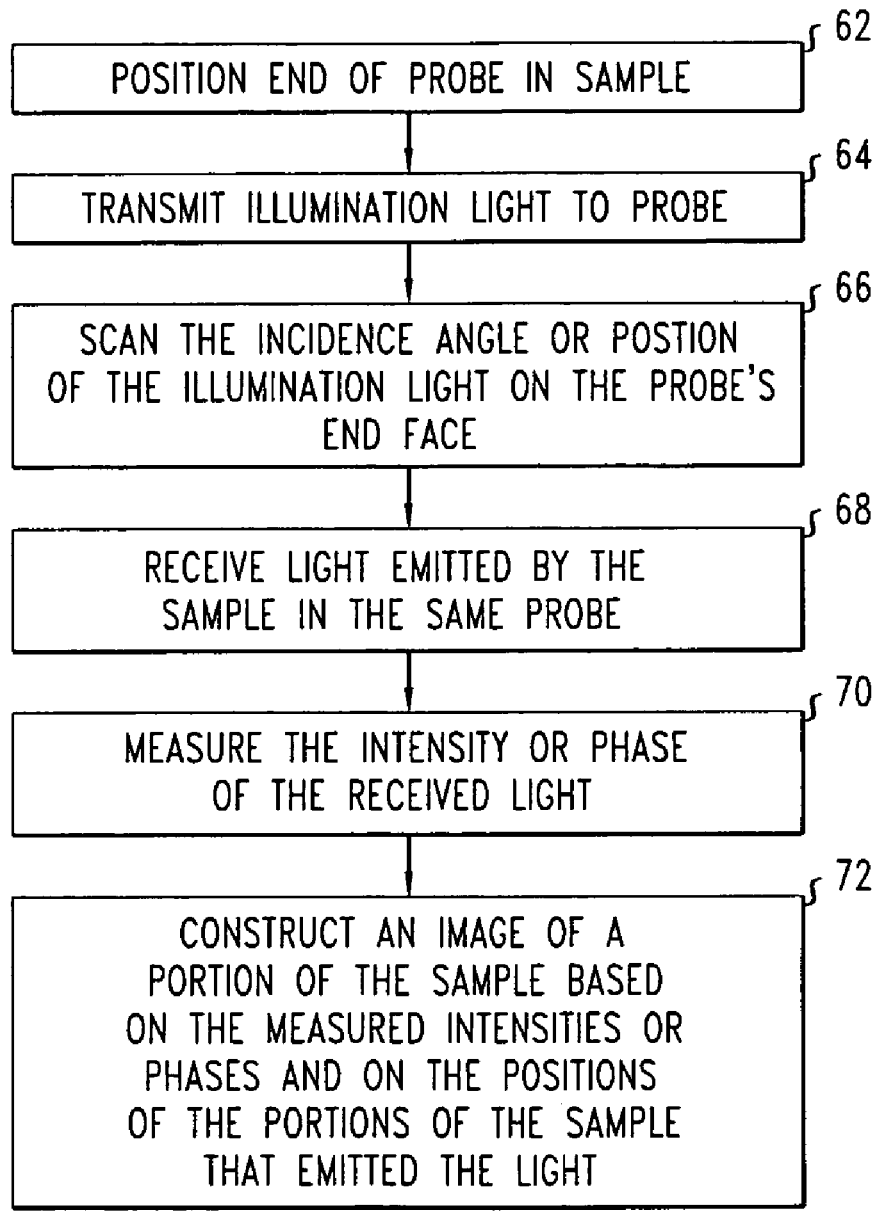
FIG. 4 is a flow chart illustrating a process for imaging a sample with the system of FIG. 3.

FIG. 4 is a flow chart that illustrates a scanning process 60 for imaging sample 40 with system 19 of FIG. 3. The process 60 includes positioning a first end of endoscopic probe 38 in the sample 40 (step 62). The process 60 also includes transmitting light, i.e., pulses, from pulsed laser 20 to insertion lens 36 and into a second end of the endoscopic probe 38 (step 64). The step of transmitting includes focusing the light onto an external end face of relay GRIN lens 37, delivering the light to objective GRIN lens 38, and emitting the light from a second end face of the objective GRIN lens 38. The second end face is located inside the sample 40.

The process 60 also includes scanning either the incidence angle or incidence position of the laser light beam on the external end face of the relay GRIN lens 37 (step 66). Scanning the incident laser light beam causes light, which is emitted from the second end face of objective GRIN lens 39, to scan a spatial region of sample 40.

The process 60 also includes receiving light that the sample 40 emits in response to being scanned in the same endoscopic probe 38 (step 68). In alternate embodiments, the light emitted by the sample 40 is collected by a second optical conduit, e.g., a single mode optical fiber or a second GRIN lens (both not shown). The process 60 also includes measuring intensity or phase of the light collected by endoscopic probe 38 in photodetector 48 (step 70). The photodetector 48 measures an optical characteristic of the light emitted by the sample 40 in response to two-photon absorption events, i.e., a characteristic of light that has a shorter wavelength than that of the pulsed laser 20. The process 60 also includes constructing a scan image of the sample 40 from the measured optical characteristic of the emitted light and the lateral coordinates of the sample regions scanned, e.g., an intensity scan image (step 72).

From the disclosure, drawings, and claims, other embodiments of the invention will be apparent to those skilled in the art.

I claim:

1. An apparatus, comprising:
   a non-fiber optical element having a first optical aperture;
   an endoscopic probe having first and second ends, the probe comprising a compound GRIN lens configured to carry illumination light along the length of the probe, the compound GRIN lens including first and second serially coupled GRIN lenses of different pitch, the first end being positioned to receive the illumination light from the first optical aperture; and
   a detector configured to measure values of a characteristic of light emitted from the first end in response to multi-photon absorption events produced by the illumination light in a sample, the detector configured to produce an output signal for a multi-photon image of the sample.

2. The apparatus of claim 1, wherein the probe further comprises a prism connected to an end of the compound GRIN lens.

3. The apparatus of claim 2, wherein the compound GRIN lens has pitch length of about one or more.

4. The apparatus of claim 1, wherein the first GRIN lens is a relay GRIN lens and the second GRIN lens is an objective GRIN lens serially coupled to the relay GRIN lens; and
   wherein the objective GRIN lens has a shorter pitch than the relay GRIN lens.

5. The apparatus of claim 4, wherein the relay GRIN lens is coupled to receive light from the first optical aperture and transmit the received light to the objective GRIN lens.

6. The apparatus of claim 4, wherein the pitch of the objective GRIN lens is at least five times shorter than the pitch of the relay GRIN lens.

7. The apparatus of claim 1, wherein the compound GRIN lens comprises:
   a relay GRIN lens; and
   an objective GRIN lens being serially coupled to one end of the relay GRIN lens; and
   a coupling GRIN lens being serially coupled to an opposite end of the relay GRIN lens as the objective GRIN lens; and wherein the objective GRIN lens and the coupling GRIN lens have shorter pitches than the relay GRIN lens.

8. The apparatus of claim 7, further comprising:

a pulsed laser; and wherein the compound GRIN lens and optical element are configured to deliver source light from the pulsed laser to the sample without the source light propagating in single mode optical fiber.

9. The apparatus of claim 1, further comprising:

a pulsed light source coupled to transmit light pulses to the optical element; and wherein the detector is configured to measure a quantity indicative of an intensity of the light emitted from the first end.

10. The apparatus of claim 9, wherein the detector is configured to measure a characteristic of light whose wavelength is shorter than a wavelength of the light produced by the source.

11. The apparatus of claim 1, further comprising:

a processor configured to produce a scan image from the measured values and estimated positions of the multi-photon absorption events.

12. The apparatus of claim 1, wherein the compound GRIN lens forms an endoscopic probe.

13. A process for scanning a region of a sample with a probe having a compound GRIN lens with first and second end faces, comprising:

positioning the first end face of the compound GRIN lens near the region of the sample, the compound GRIN lens including first and second serially coupled GRIN lenses of different pitch;

transmitting light to the second end face of the compound GRIN lens such that the compound GRIN lens carries the light along the length of the probe; and scanning one of an incidence position and an incidence angle of the light on the second end face of the compound GRIN lens while performing the transmitting to generate a scan of the region of the sample.

14. The process of claim 13, further comprising:

receiving light emitted by the region of the sample in response to the scanning; and measuring values of a quantity indicative of an intensity or a phase of the emitted light in response to the receiving.

15. The process of claim 14, further comprising:

forming an image of the region of the sample from the measure values and positions of portions of the sample that produced the emitted light.

16. The process of claim 14, wherein the receiving comprises collecting the emitted light through the first end face of the compound GRIN lens.

17. The process of claim 14, wherein the quantity is indicative of the intensity of the emitted light.

18. The process of claim 14, wherein the transmitting comprises sending a series of pulses of laser light to the second end face.

19. The process of claim 14, wherein the measuring includes determining the values of the quantity for light whose wavelength is shorter than the wavelength of the transmitted light.

20. The process of claim 13, wherein the positioning causes the first end face to be located in the sample and the second face to be located outside the sample.

21. The process of claim 13, wherein the act of transmitting causes the transmitted light to be transmitted through a relay GRIN lens and then, to be transmitted through an objective GRIN lens that is serially coupled to one end of the relay GRIN lens.

* * * * *